US012616429B2

(12) United States Patent
Schaer et al.

(10) Patent No.: US 12,616,429 B2
(45) Date of Patent: May 5, 2026

(54) SYSTEM AND APPARATUS FOR PRE-COLLIMATION OF A RADIATION BEAM

(71) Applicant: Siemens Healthineers International AG, Steinhausen (CH)

(72) Inventors: Niklaus Schaer, Wikon (CH); Juerg Zinniker, Aarau (CH); Mathieu Plamondon, Glattbrugg (CH); Konrad Fellmann, Baden (CH)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 312 days.

(21) Appl. No.: 18/467,944

(22) Filed: Sep. 15, 2023

(65) Prior Publication Data

US 2025/0090114 A1     Mar. 20, 2025

(51) Int. Cl.
| | |
|---|---|
| *A61B 6/00* | (2024.01) |
| *A61B 6/06* | (2006.01) |
| *A61B 6/40* | (2024.01) |
| *A61B 6/03* | (2006.01) |

(52) U.S. Cl.
CPC .............. *A61B 6/4035* (2013.01); *A61B 6/06* (2013.01); *A61B 6/032* (2013.01)

(58) Field of Classification Search
CPC ... A61B 6/06; A61B 6/4042; A61B 2562/185; G21K 1/04; G21K 1/025; G21K 1/046;
G21K 5/04; G21K 5/10; A61N 2005/1094; A61N 5/10; A61N 5/1045;
G02B 6/2937; G02B 5/28; G02B 27/30
See application file for complete search history.

(56) References Cited

U.S. PATENT DOCUMENTS

| | | | |
|---|---|---|---|
| 2006/0097197 A1 | 5/2006 | Sakaguchi | |
| 2006/0113466 A1 | 6/2006 | Kabasawa et al. | |
| 2013/0221243 A1 | 8/2013 | Perkins | |
| 2019/0099622 A1 | 4/2019 | Filiberti | |
| 2020/0312478 A1* | 10/2020 | Sutter | A61B 6/06 |
| 2023/0270392 A1 | 8/2023 | Nayak et al. | |

FOREIGN PATENT DOCUMENTS

| | | | | |
|---|---|---|---|---|
| CN | 209074650 U | * | 7/2019 | |
| EP | 3777687 A1 | * | 2/2021 | A61B 6/4429 |
| WO | 2013180883 A1 | | 12/2013 | |

OTHER PUBLICATIONS

Konston, K. et al., "Characterization of scatter magnitude and distribution in dedicated breast computed tomography with bowtie filters," Journal of Medical Imaging, Oct.-Dec. 2014.
Anonymous, "Shadow play—Wikipedia," pp. 1, 6, 9 and 11, Sep. 9, 2023.

* cited by examiner

*Primary Examiner* — Don K Wong
(74) *Attorney, Agent, or Firm* — Harness, Dickey & Pierce, P.L.C.

(57) ABSTRACT

An apparatus includes a pre-collimator and a shape filter. The shape filter is in at least a first portion of a first part of the pre-collimator.

16 Claims, 8 Drawing Sheets

SYSTEM AND APPARATUS FOR PRE-COLLIMATION OF A RADIATION BEAM

FIELD

The present disclosure relates to a system and apparatus for pre-collimation of a radiation beam.

BACKGROUND

In medical imaging, such as computed tomography (CT), filters may be used to modify the intensity and/or change the shape of a radiation beam.

SUMMARY

In at least one example embodiment, the present disclosure provides an apparatus. The apparatus includes a pre-collimator and a shape filter in at least a first portion of a first part of the pre-collimator.

In at least one example embodiment, the first part of the pre-collimator is configured to move between a first position and a second position. The first portion is aligned with a central beam axis of a radiation beam in the first position and the first portion is out of the radiation beam in the second position.

In at least one example embodiment, the pre-collimator includes a second part of the pre-collimator. The second part of the pre-collimator is aligned with the central beam axis.

In at least one example embodiment, the second part of the pre-collimator is fixed with respect to the radiation beam.

In at least one example embodiment, the first part of the pre-collimator includes a second portion. The second portion is similar to the first portion of the pre-collimator.

In at least one example embodiment, the second portion is aligned with the central beam axis of the radiation beam and the first portion is out of the radiation beam when the first part is in the second position. The second portion is out of the radiation beam and the first portion is aligned with the central beam axis of the radiation beam when the first part is in the first position.

In at least one example embodiment, the apparatus further includes a mount configured to hold the first portion and the second portion of the pre-collimator.

In at least one example embodiment, the mount is configured to move between the first position and the second position. When the mount is in the first position, the first portion of the pre-collimator is aligned with the central beam axis. When the mount is in the second position, the second portion of the pre-collimator is aligned with the central beam axis.

In at least one example embodiment, the apparatus further includes a first beam hardening filter coupled to the mount adjacent the first portion of the pre-collimator and a second beam hardening filter coupled to the mount adjacent the second portion of the pre-collimator.

In at least one example embodiment, the second part of the pre-collimator is closer to a source of radiation than the first part of the pre-collimator.

In at least one example embodiment, the shape filter includes a first surface and a second surface opposite the first surface. The first surface includes a curved surface configured to face a radiation source and the second surface comprises a planar surface.

In at least one example embodiment, the present disclosure provides a system. The system includes a radiation source configured to emit a radiation beam and a filtering assembly. The filtering assembly including a pre-collimator and a shape filter in at least a first portion of a first part of the pre-collimator.

In at least one example embodiment, the first part of the pre-collimator is configured to move between a first position and a second position. The first portion is aligned with a central beam axis of the radiation beam in the first position and the first portion is out of the radiation beam in the second position.

In at least one example embodiment, the pre-collimator includes a second part of the pre-collimator. The second part of the pre-collimator is aligned with the central beam axis.

In at least one example embodiment, the second part of the pre-collimator is fixed with respect to the radiation beam.

In at least one example embodiment, the first part of the pre-collimator includes a second portion. The second portion is similar to the first portion of the pre-collimator.

In at least one example embodiment, the second portion is aligned with the central beam axis of the radiation beam and the first portion is out of the radiation beam when the first part is in the second position. The second portion is out of the radiation beam and the first portion is aligned with the central beam axis of the radiation beam when the first part is in the first position.

In at least one example embodiment, the system further includes a mount configured to hold the first portion and the second portion of the pre-collimator.

In at least one example embodiment, the mount is configured to move between the first position and the second position. When the mount is in the first position, the first portion of the pre-collimator is aligned with the central beam axis. When the mount is in the second position, the second portion of the pre-collimator is aligned with the central beam axis.

In at least one example embodiment, the system further includes a first beam hardening filter coupled to the mount adjacent the first portion of the pre-collimator and a second beam hardening filter coupled to the mount adjacent the second portion of the pre-collimator.

In at least one example embodiment, the second part of the pre-collimator is closer to the radiation source than the first part of the pre-collimator.

In at least one example embodiment, the shape filter includes a first surface and a second surface opposite the first surface. The first surface includes a curved surface configured to face the radiation source and the second surface comprises a planar surface.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION OF EXAMPLE EMBODIMENTS

Figure 1:
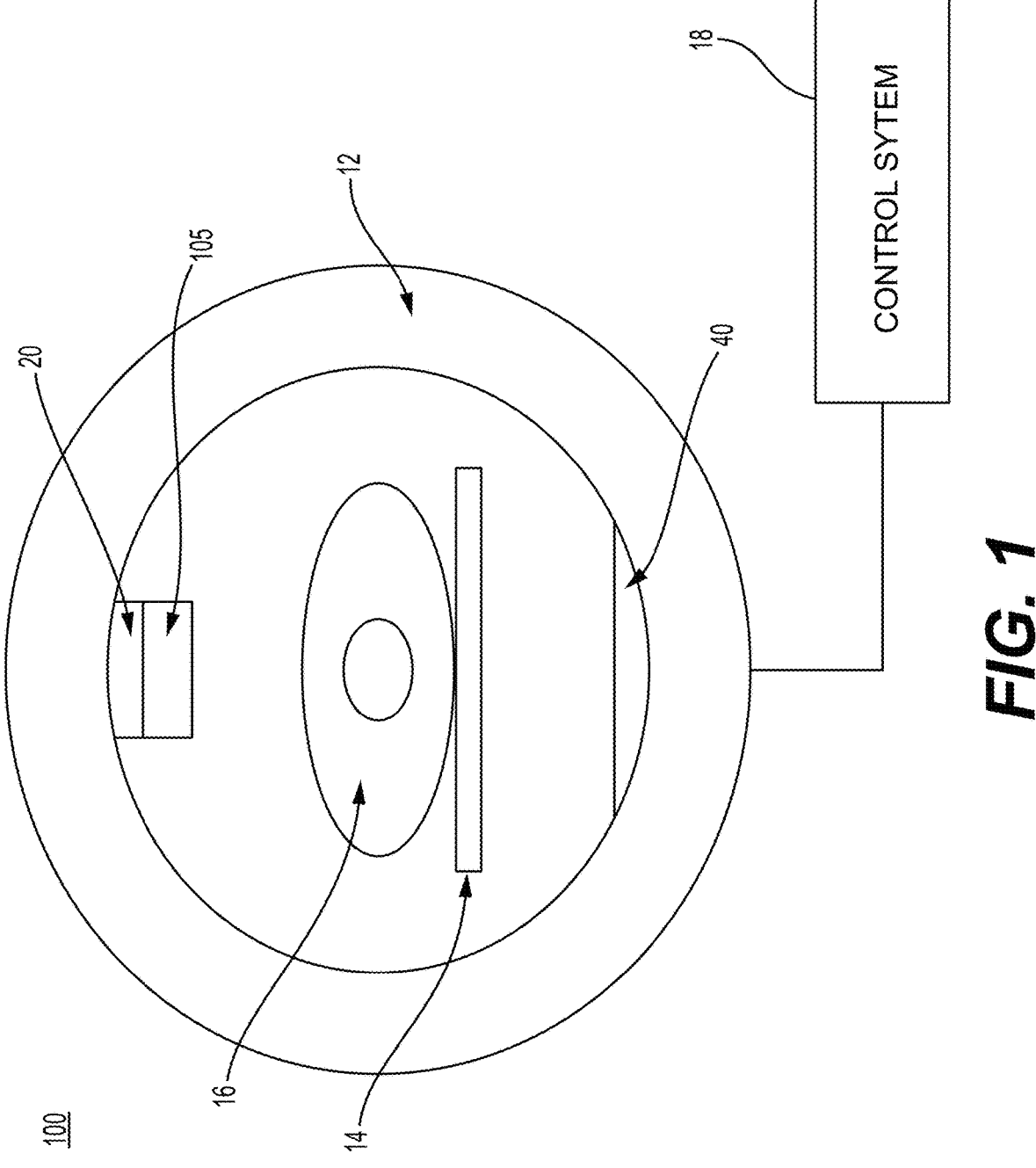
FIG. 1 is a front view of an imaging system, according to at least one example embodiment.

Independent of the grammatical term usage, individuals with male, female or other gender identities are included within the term.

Some detailed example embodiments are disclosed herein. However, specific structural and functional details disclosed herein are merely representative for purposes of describing some example embodiments. Example embodiments may, however, be embodied in many alternate forms and should not be construed as limited to only example embodiments set forth herein.

Accordingly, while example embodiments are capable of various modifications and alternative forms, example embodiments thereof are shown by way of example in the drawings and will herein be described in detail. It should be understood, however, that there is no intent to limit an example embodiment to the particular forms disclosed, but to the contrary, example embodiments are to cover all modifications, equivalents, and alternatives falling within the scope of an example embodiment. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/ or" includes any and all combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiment.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiment only and is not intended to be limiting of example embodiment. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, and/or elements, but do not preclude the presence or addition of one or more other features, integers, steps, operations, elements and/or groups thereof.

Example embodiments are described herein with reference to cross-sectional illustrations that are schematic illustrations of example embodiment. As such, variations from the shapes of the illustrations are to be expected. Thus, example embodiment should not be construed as limited to the shapes of regions illustrated herein but are to include deviations and variations in shapes.

When the words "about" and "substantially" are used in this specification in connection with a numerical value, it is intended that the associated numerical value include a tolerance of ±10% around the stated numerical value, unless otherwise explicitly defined. Moreover, when the terms "generally" or "substantially" are used in connection with geometric shapes, it is intended that precision of the geometric shape is not required but that latitude for the shape is within the scope of the disclosure. Furthermore, regardless of whether numerical values or shapes are modified as "about," "generally," or "substantially," it will be understood that these values and shapes should be construed as including a manufacturing or operational tolerance (e.g., ±10%) around the stated numerical values or shapes.

Unless otherwise defined, all terms (including technical and scientific terms) used herein have the same meaning as commonly understood by one of ordinary skill in the art to which example embodiment belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1 is a front view of an imaging system, according to at least one example embodiment.

In at least one example embodiment, an imaging system 100 may be used for diagnosis and treatment. For example, the imaging system 100 may include a computed tomography (CT) system to scan objects and/or a human patient. In at least one example embodiment, the imaging system 100 includes a support 14 for an object or patient, such as a subject 16, to be imaged or scanned and/or treated. For example, the support 14 may include a table or bed.

In at least one example embodiment, the imaging system 100 includes a radiation source 20. The radiation source 20 may be coupled to a gantry 12 and positioned above the support 14 and/or the subject 16. The gantry 12 may configured to rotate about the support 14 and/or the subject 16 and move back and forth along a length of the support 14. The radiation source 20 is configured to direct a radiation beam towards a target, such as the subject 16, and through to a detector 40. The detector 40 includes a plurality of sensors configured to detect or sense an intensity or energy level of the radiation beam that passes through the subject 16. In at least one example embodiment, the imaging system 100 also includes a control system 18 configured to control operation of the gantry 12 and the radiation source 20. For example, the control system 18 may be configured to control the energy level of the radiation beam emitted from the radiation source 20.

In at least one example embodiment, the imaging system 100 includes a filtering assembly 105. The filtering assembly 105 may be positioned adjacent the radiation source 20, as will be discussed below with respect to FIGS. 2A-2B.

Figure 2A:
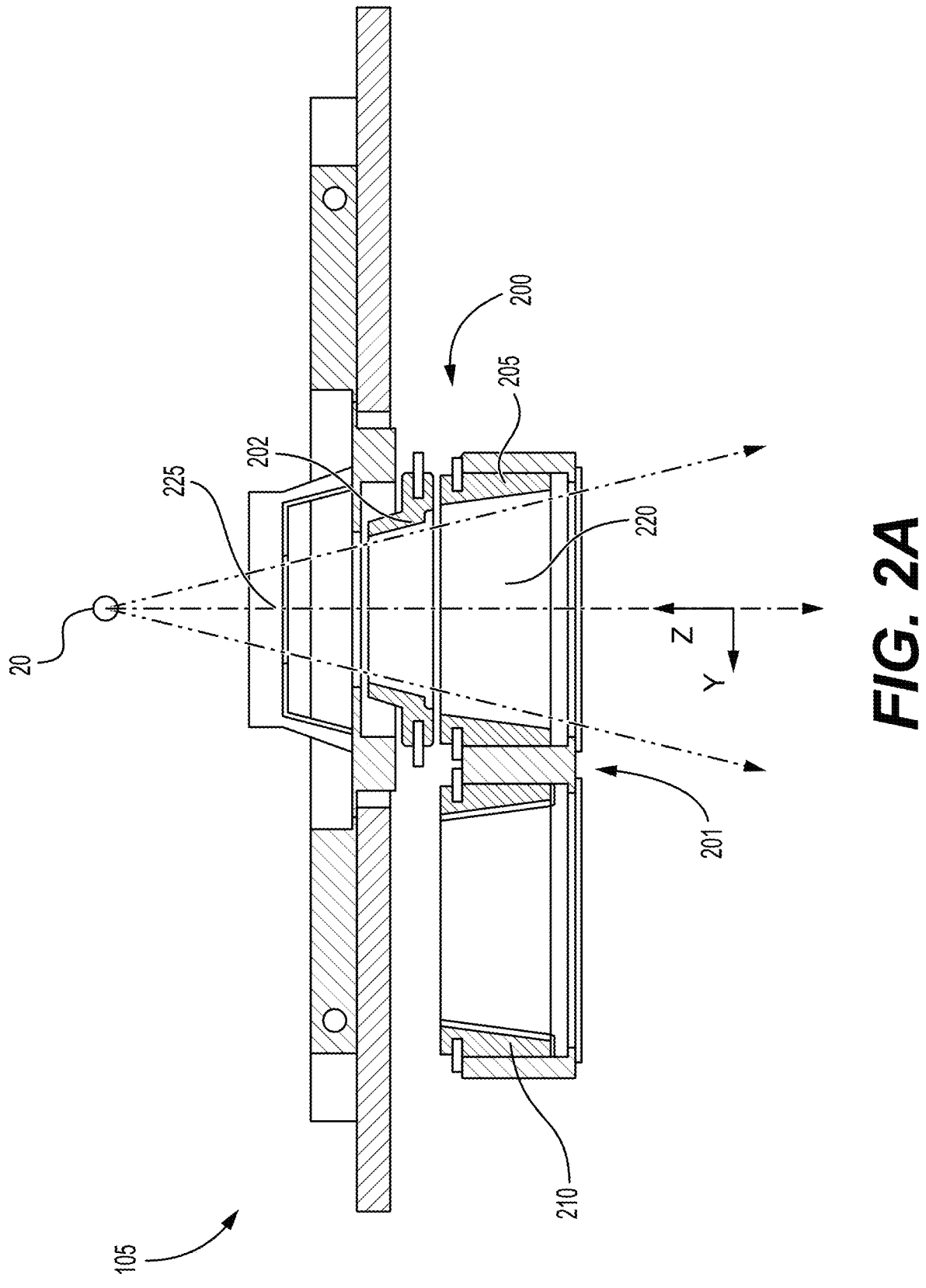
FIG. 2A is a cross-section view of the imaging system of FIG. 1 with a pre-collimator in a first position, according to at least one example embodiment.
Figure 2B:
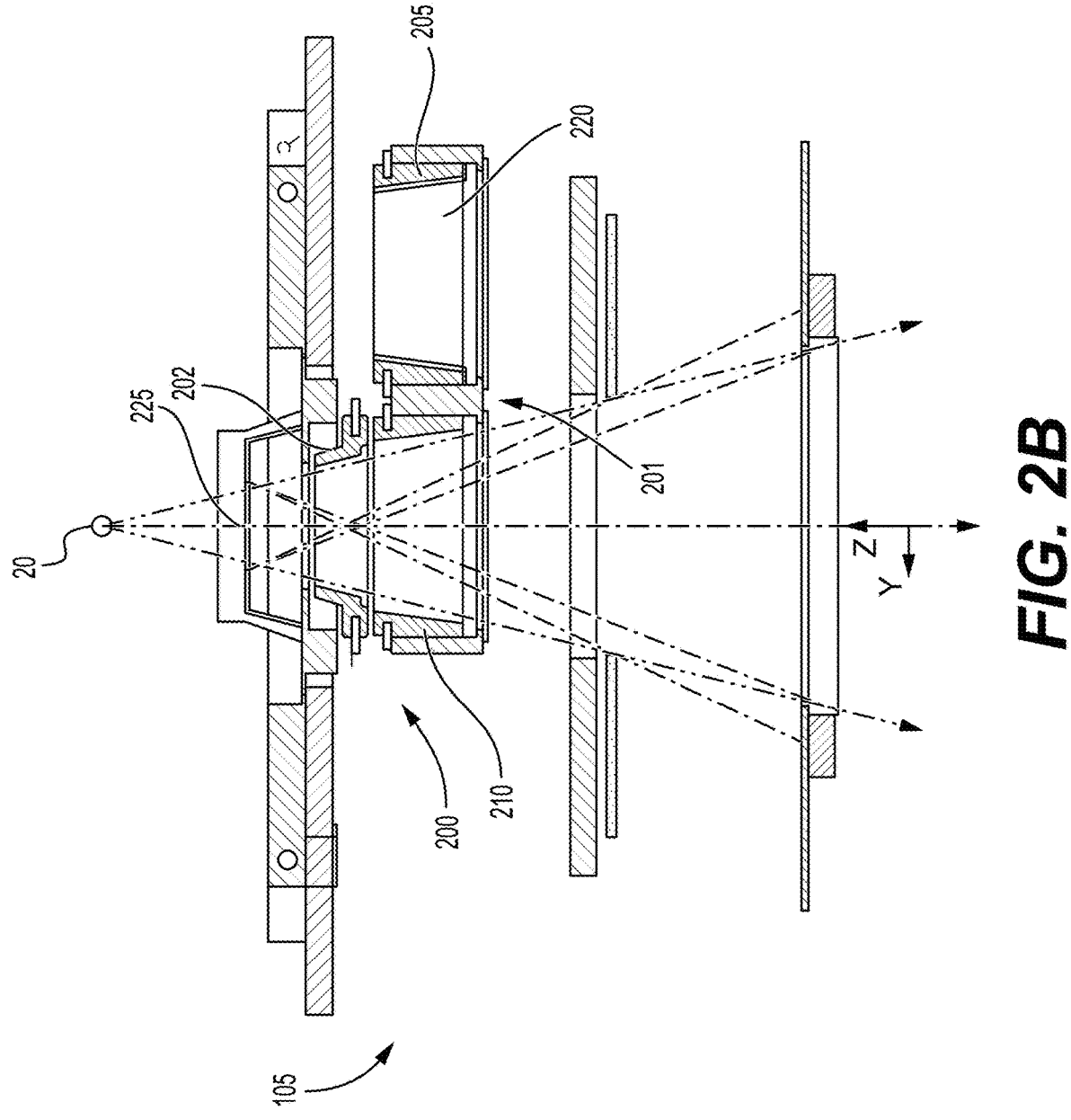
FIG. 2B is a cross-section view of the imaging system of FIG. 1 with the pre-collimator in a second position, according to at least one example embodiment.

FIG. 2A is a cross-section view of the imaging system of FIG. 1 with a pre-collimator in a first position, according to at least one example embodiment. FIG. 2B is a cross-section view of the imaging system of FIG. 1 with the pre-collimator in a second position, according to at least one example embodiment.

In at least one example embodiment, the filtering assembly 105 includes a pre-collimator 200 and a beam-shaping filter, such as a shape filter 220. The pre-collimator 200 includes a moveable part, such as a first part 201, and a fixed part, such as a second part 202. In at least one example embodiment, the second part 202 of the pre-collimator 200 is coupled to or positioned adjacent the radiation source 20. For example, the second part 202 of the pre-collimator 200 may be closer to the radiation source 20 than the first part 201. The second part 202 may be aligned with a central beam axis 225 of the radiation beam from the radiation source 20. For example, a vertical line extending through the z-axis and through a center of the first part 201 may be aligned with the central beam axis 225 of the radiation beam. As indicated above, the second part 202 may also be fixed with respect to the radiation source 20 and the radiation beam.

In at least one example embodiment, the first part 201 includes a first portion 205 and a second portion 210. The first portion 205, the second portion 210, and the second part 202 may be the same or similar. In other example embodiments, the first portion 205 and the second portion 210 are the same or similar. For example, the second portion 210 may have a similar size and shape as the first portion 205. In at least one example embodiment, the pre-collimator 200, including the first portion 205, the second portion 210, and the second part 202, comprises lead, brass, or a combination thereof. The first portion 205, the second portion 210, and the second part 202 of the pre-collimator 200 may be configured to contain scatter emitted in the transversal direction. For example, the first portion 205, the second portion 210, and the second part 202 of the pre-collimator 200 may block off-focal radiation; scatter produced in a front window of a tube of the radiation source; any punch-through and scatter from a diaphragm of the radiation source; and/or one or more filters, beam-shaping elements, and blades associated with the imaging system 100.

In at least one example embodiment, the first portion 205 of the pre-collimator 200 includes the shape filter 220. For example, the shape filter 220 may be a bowtie filter. In other example embodiments, the shape filter 220 may include a triangular, trapezoidal, or wedge-shaped beam-shaping filter. The shape filter 220 may be configured to reduce the exposure of the radiation beam to the subject 16 and improve scatter behavior of the radiation beam delivered to the detector 40, as will be discussed in more detail with respect to FIG. 4, below. In at least one example embodiment, the shape filter 220 comprises aluminum, tantalum, lead, brass, a plastic material or a combination thereof.

In at least one example embodiment, the first part 201 of the pre-collimator 200, including the first portion 205 and the second portion 210, is configured to be movably coupled to the second part 202 of the pre-collimator 200. For example, the first portion 205 and the second portion 210 may be moveable between a first position and a second position. In the first position, the first portion 205 is aligned with the central beam axis 225 of the radiation beam and the third portion is out of the radiation beam such that the second portion 210 is not aligned with the central beam axis 225. For example, a vertical line extending through the z-axis and through a center of the first portion 205 is aligned with the central beam axis 225 in the first position, as shown in FIG. 2A. In the second position, the second portion 210 is aligned with the central beam axis 225 and the first portion 205 is out of the radiation beam such that the first portion 205 is not aligned with the central beam axis 225. For example, a vertical line extending though the z-axis and through a center of the second portion 210 is aligned with the central beam axis 225 in the second position, as shown in FIG. 2B. The first portion 205 and the second portion 210 may slide between the first position and the second position to engage with the second portion 210 of the pre-collimator 200.

In at least one example embodiment, an operator may manually slide the first portion 205 and the second portion 210 between the first position and the second position. Accordingly, the operator may select whether to align the first portion 205 and the shape filter 220 with the central beam axis 225 or the second portion 210 with the central beam axis 225 based on a selected radiation procedure or to suit a particular need. In other example embodiments, the first portion 205, the second portion 210, and the shape filter 220 may be moved between the first position and the second position, such as by a linear actuator. The linear actuator and/or the first portion 205 and the second portion 210 may be communicatively coupled to the control system 18 to control movement of the first portion 205 and the second portion 210 between the first position and the second position. For example, the control system 18 may control movement of the first portion 205, the second portion 210, and the shape filter 220 based on the two-dimensional or three-dimensional image to be acquired.

Figure 3:
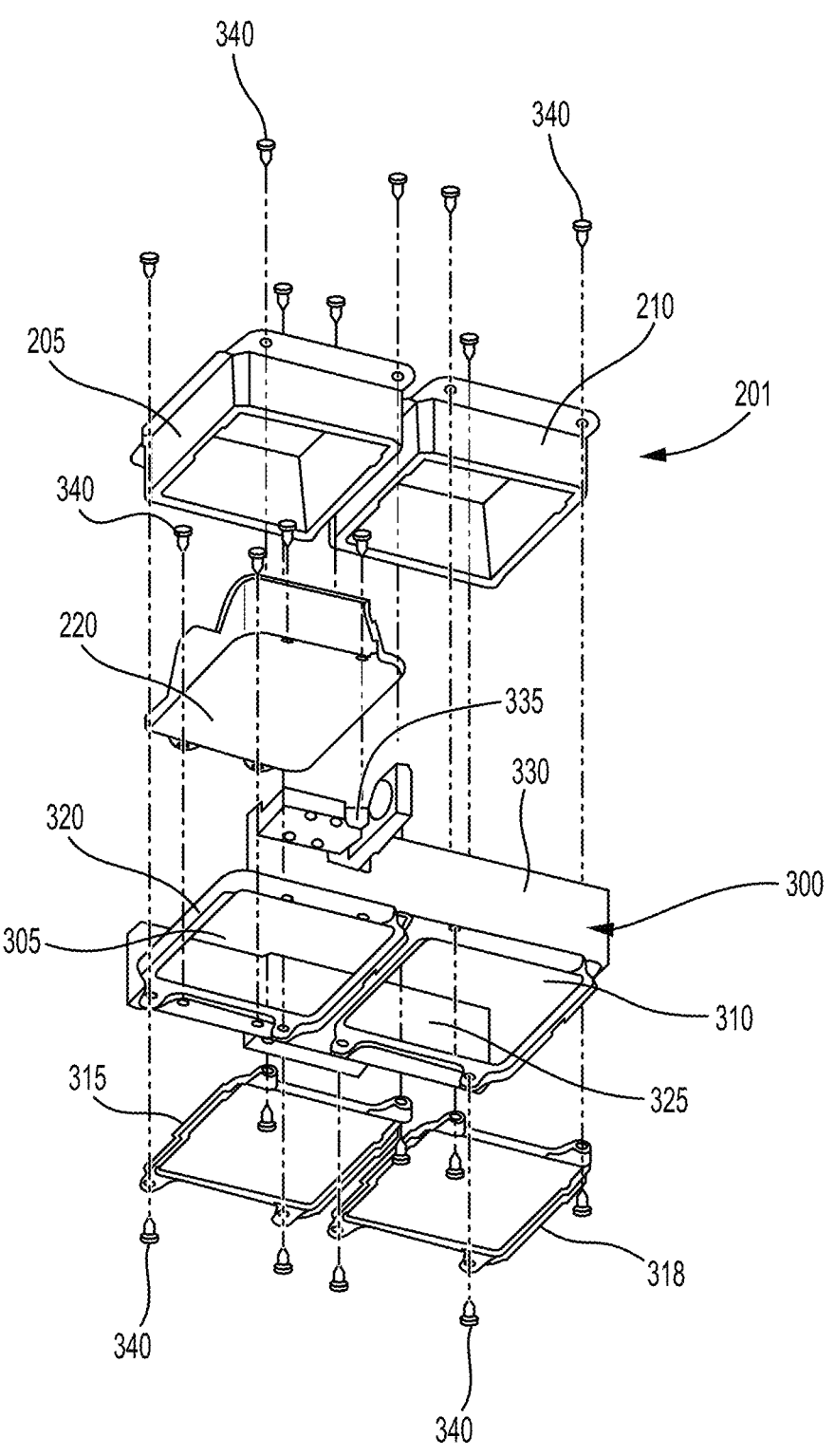
FIG. 3 is an exploded view of a first part of the pre-collimator of FIGS. 2A-2B, according to at least one example embodiment.

FIG. 3 is an exploded view of a first part of the pre-collimator of FIGS. 2A-2B, according to at least one example embodiment.

In at least one example embodiment, the filtering assembly 105 includes a mount 300 configured to hold the first part 201 of the pre-collimator 200. For example, the mount 300 may hold the first portion 205 and the second portion 210 of the first part 201 of the pre-collimator 200. The mount 300 may include a base portion 320 defining a first opening 305 configured to receive at least a portion of the first portion 205 of the pre-collimator 200 and a second opening 310 configured to receive at least a portion of the second portion 210 of the pre-collimator 200. The first opening 305 of the mount 300 may also receive at least a portion of the shape filter 220. In at least one example embodiment, the mount 300 is moveably coupled to the second portion 210 of the pre-collimator 200 and configured to move the first portion 205, including the shape filter 220, and the second portion 210 between the first position and the second position, as discussed with respect to FIGS. 2A-2B.

In at least one example embodiment, the mount 300 includes a first sidewall 325 and a second sidewall 330. The first sidewall 325 and the second sidewall 330 may be positioned on opposing sides of the base portion 320. The first sidewall 325 and the second sidewall 330 may each extend along a length of the base portion 320 and have a height extending perpendicular to the base portion 320. The first sidewall 325 and the second sidewall 330 may be configured to support the first portion 205 and the second portion 210 and/or secure the first portion 205 and the second portion 210 to the mount 300.

In at least one example embodiment, the mount 300 may include one or more attachment features 335. For example, the one or more attachment features 335 may include one or more brackets connected to one or both of the first sidewall 325 and the second sidewall 330. The one or more attachment features 335 may also be configured to couple the mount 300 to at least a portion of the imaging system 100, such as the gantry 12 or the radiation source 20.

In at least one example embodiment, the filtering assembly 105 may include a plurality of fasteners 340, such as bolts and/or screws, for connecting the first portion 205, the second portion 210, and the shape filter 220 to the mount 300.

In at least one example embodiment, the filtering assembly 105 may include one or more additional filters coupled to the first portion 205, the second portion 210, and/or the mount 300. For example, the filtering assembly 105 may include a first filter 315 coupled to a side of the mount 300 opposite the first portion 205 and a second filter 318 coupled to a side of the mount opposite the second portion 210. For example, the first filter 315 and the second filter 318 may be coupled to the mount 300 by one or more of the fasteners 340. In at least one example embodiment, the first filter 315 may define an opening corresponding to the first opening 305 of the mount 300 and the second filter 318 may define an opening corresponding to the second opening 310 of the mount 300. In other example embodiments, the first filter 315 and the second filter 318 are configured to cover the first opening 305 and the second opening 310, respectively, In at least one example embodiment, the first portion 205 and the second portion 210 may comprise additional filters, combinations of filters, or sizes of filters. For example, the first filter 315 and/or the second filter 318 may comprise flat filters and/or beam hardening filters. A beam hardening filter, such as a foil filter, may be used to change the energy spectrum of the radiation beam. For example, a beam hardening filter can be used to filter out lower energy X-rays, changing the X-ray spectrum to a "harder" beam with a larger proportion of higher energy X-rays. The lower energy X-rays tend to get absorbed by the subject 16 and thus do not reach the detector 40 (and hence do not contribute to the resultant image), and so only increase the dose to the subject 16. By hardening the beam, the dose to the subject 16 can be reduced. For example, higher energy X-rays have an increased probability of penetrating the subject 16 without reducing the dose delivered to the subject 16. Accordingly, higher energy X-rays have an increased probability of penetrating the subject 16 and less flux is needed to get a desired signal on the detector 40. Without hardening the radiation beam before it reaches the subject 16, low energy photons penetrate at least partially into the subject 16 and provide a large dosage of radiation.

In at least one example embodiment, the first filter 315 and the second filter 318 may comprise a foil of titanium, tin, copper, or a combination thereof. For example, the first filter 315 and/or the second filter 318 may include a copper foil between about 0.2 mm and about 0.3 mm thick. In other example embodiments, the first filter 315 and/or the second filter 318 may comprise a High-Z material.

Figure 4:
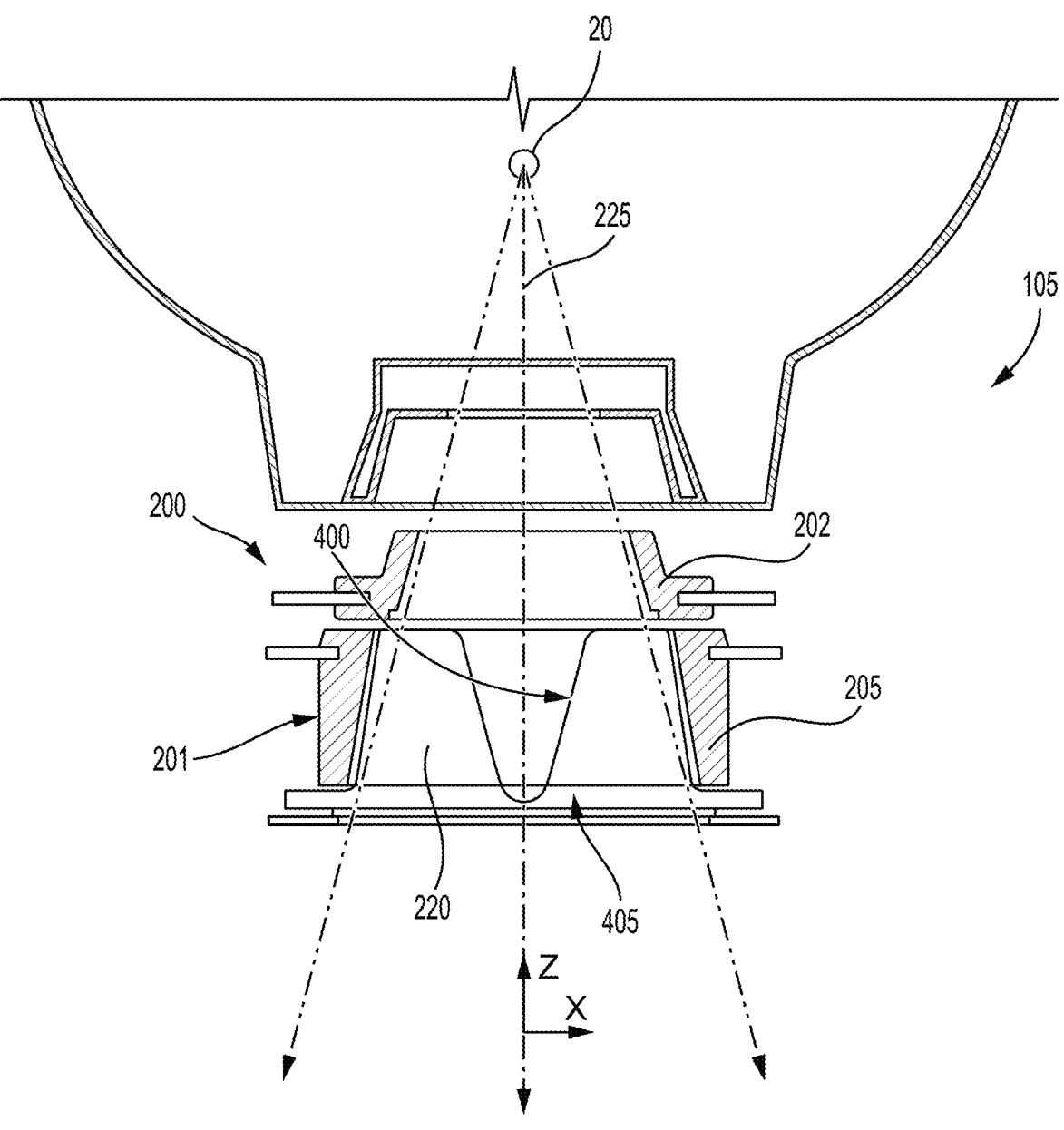
FIG. 4 is a side, cross-section view of the imaging device of FIG. 1 with the pre-collimator, according to at least one example embodiment.

FIG. 4 is a side, cross-section view of the imaging device of FIG. 1 with the pre-collimator, according to at least one example embodiment.

In at least one example embodiment, the shape filter 220 includes a first surface 400 and a second surface 405 opposite the first surface 400. The first surface 400 includes a curved surface. The curved surface is configured to face the radiation source 20 such that a bottom of the curved surface is further from the radiation source 20, as shown in FIG. 4. The second surface 405 of the shape filter 220 includes a flat or planar surface configured to face the subject 16. In other example embodiments, the first surface 400, including the curved surface, may be configured to face the subject 16 and the second surface 405, including the planar surface, may be configured to face the radiation source 20.

In at least one example embodiment, the shape filter 220 is configured to shape the radiation beam such that the shape of the radiation beam may be more suitable for the cylindrical geometry of the subject 16, such as a patient, to be imaged. The shape filter 220 is also configured to shape the radiation beam such that transversal or lateral scatter of the radiation beam is reduced. For example, the shape filter 220 may concentrate the radiation beam closer to the central beam axis 225 and reduce the scatter of the radiation beam outside the subject 16. Thus, the scatter caused by the shape filter 220 has a smaller footprint.

Combining the shape filter 220 within the pre-collimator 200 provides a more compact system and allows the shape filter 220 to be positioned closer to the radiation source 20 compared to shape filters that must be larger in size when they are positioned further downstream of the radiation beam and further from the radiation source 20. Placing the shape filter 220 closer to the radiation source 20 also allows the shape filter 220 to have a smaller size, which provides less weight and reduced costs for manufacturing. Ease of manufacturing of the shape filter 220 may also be improved because only the first surface 400 of the shape filter 220 includes the curved surface and the second surface 405 of the shape filter 220 is flat or planar. Thus, machining only needs to be performed on one side of the shape filter 220. Additionally, a filter, such as the first filter 315 or the second filter 318, may be placed directly on the planar, second surface 405 of the shape filter 220, which may reduce the overall footprint and the complexity of the filtering assembly 105.

Positioning the shape filter 220 close to the radiation source 20, reducing the size of the shape filter 220, and providing a flat or planar surface on the second surface 405 may also improve scatter modeling and image reconstruction. Because the shape filter 220 is close to the radiation source 20, the scatter of the radiation beam is not as dependent on blades of a collimator that may be positioned downstream of the shape filter 220 along the path of the radiation beam. Any residual scatter emitted transversely or laterally from the shape filter 220 may also be blocked by at least the first portion 205 of the pre-collimator 200.

Scatter modeling and image reconstruction is improved because, due to the shape of the shape filter 220 and the position of the shape filter 220 close to the radiation source 20, it can be assumed that any remaining scatter will be closer to the primary beam of the radiation beam, such as close to the central beam axis 225. This assumption simplifies software correction steps because scatter from the shape filter 220 has been spatially limited, creating less noise outside the subject 16 and away from the central beam axis 225, and can be corrected by software quicker and easier, resulting in a more accurate image.

Figure 5A:
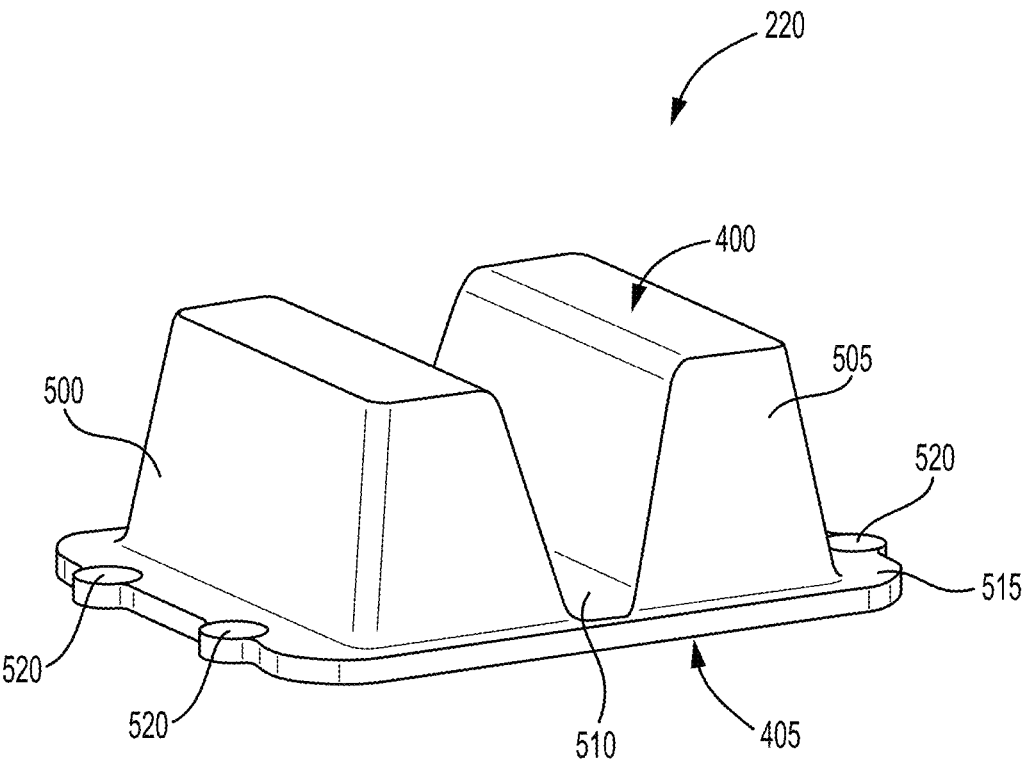
FIG. 5A is a perspective view of a shape filter of the pre-collimator of FIGS. 2A-4, according to at least one example embodiment.
Figure 5B:
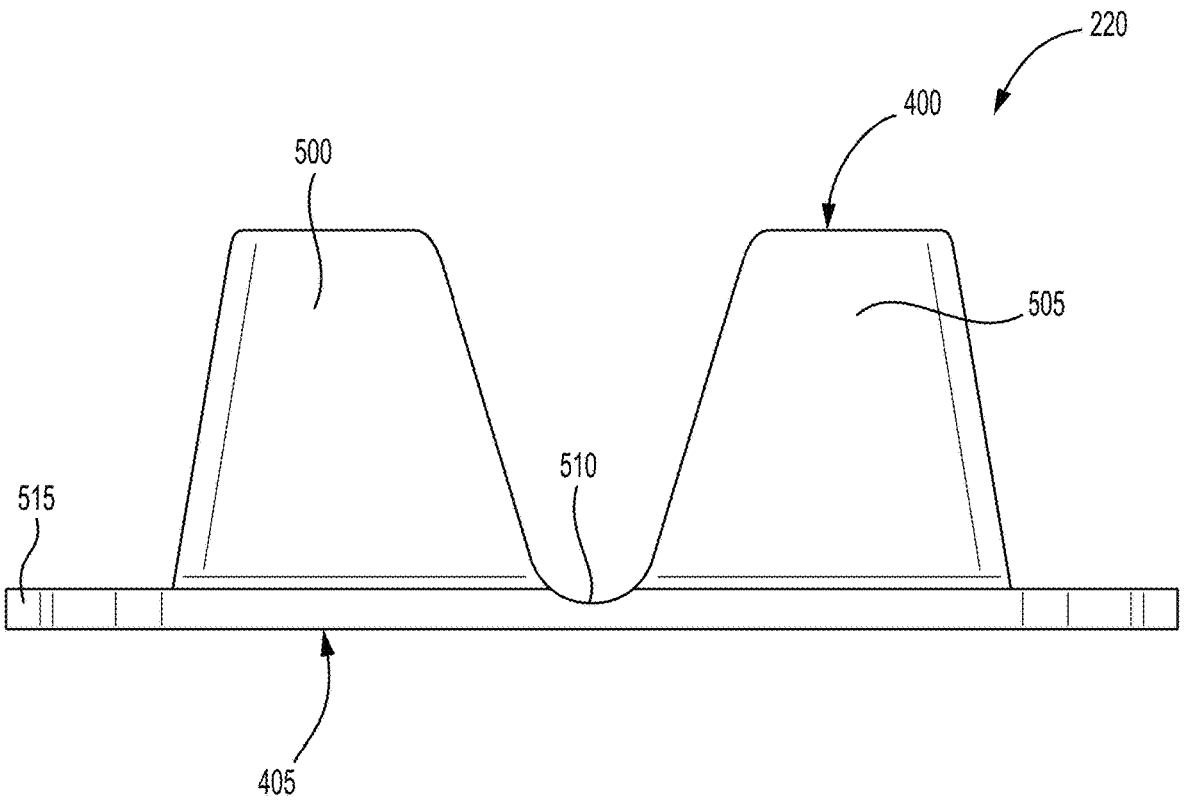
FIG. 5B is a side view of the shape filter of FIG. 5A, according to at least one example embodiment.
Figure 5C:
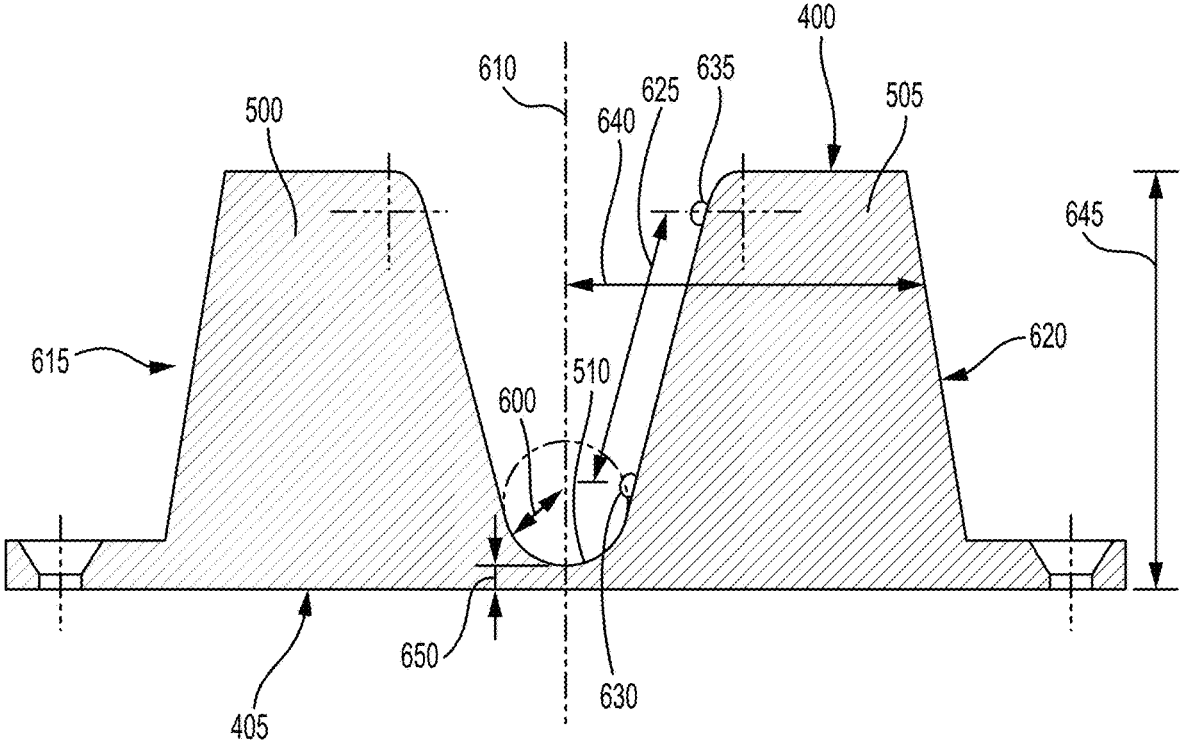
FIG. 5C is a cross-section view of the shape filter of FIG. 5B, according to at least one example embodiment.

FIG. 5A is a perspective view of a shape filter of the pre-collimator of FIGS. 2A-4, according to at least one example embodiment. FIG. 5B is a side view of the shape filter of FIG. 5A, according to at least one example embodiment. FIG. 5C is a cross-section view of the shape filter of FIG. 5B, according to at least one example embodiment.

In at least one example embodiment, the shape filter 220 includes a first region 500, a second region 505, and a third region 510. The third region 510 includes the curved surface and may be between the first region 500 and the second region 505, as shown in FIGS. 5A-5C. In at least one example embodiment, the first surface 400 of the first region 500 and the second region 505 include a flat or planar surface. For example, at least a portion of the first surface 400 of the first region 500 and the second region 505 may be parallel with the second surface 405. In other example embodiments, at least a portion of the first surface 400 of the first region 500 and the second region 505 may be curved or rounded.

In at least one example embodiment, the shape filter 220 may include a flange portion 515. The flange portion 515 may extend around at least a portion of a perimeter of the shape filter 220. For example, the flange portion 515 may extend around the perimeter of the second surface 405 of the shape filter 220. In other example embodiments, the flange portion 515 may extend from opposing ends of the shape filter 220. For example, the flange portion 515 may extend from the second surface 405 adjacent the first region 500 and/or the second surface 405 adjacent the second region 505. The flange portion 515 may be configured to secure the shape filter 220 to the first portion 205 and/or the mount 300. For example, as shown in FIG. 4, the flange portion 515 may be coupled to an end of the first portion 205. Additionally or alternatively, the flange portion 515 may be coupled to at least a portion of an interior surface of the base portion 320 of the mount 300, as shown in FIG. 3. For example, the flange portion 515 may define one or more through-holes 520 for receiving the fasteners 340 and securing the shape filter 220 to the first portion 205 and/or the mount 300.

With reference to FIG. 5C, the third region 510 of the shape filter 220 includes the curved surface. In at least one example embodiment, a base of the curved surface, or the third region 510, may be defined by a circle having a radius 600 between about 0 cm and about 20 cm. In at least one example embodiment, the radius 600 may be about 0.5 cm. The radius 600 may be defined between an inner surface of the curved surface of the third region 510 and a vertical axis 610 extending through a center of the shape filter 220. In at least one example embodiment, the curved portion of the first region 500 and the second region 505 may taper outwardly from the third region 510 into the flat or planar surface of the first surface 400, as shown in FIGS. 5A-5C.

In at least one example embodiment, the shape filter 220 includes a distance 625 between a first inflection point 630, where the slope between the base of the third region 510 towards the second region 505 varies, and a second inflection point 635, where the slope between the curved surface of the third region 510 towards a top of the second region 505 varies. The distance 625 may be between about 0 cm and about 20 cm. The distance 625 may also vary based on a desired thickness or height of the shape filter 220, which is described below. In at least one example embodiment, the distance 625 may be the same between the base of the third region 510 and a top of the first region 500.

In at least one example embodiment, a slope of the first surface 400 between the third region 510 and the second region 505 and a slope between the third region 510 and the first region 500 gradually terminates at a base of the curved surface of the third region 510. The gradual slope and positioning the curved surface of the shape filter facing the radiation source 20 allows the base of the curved surface to be as far away as possible from the radiation source 20, which mitigate issues with sensitivity to the focus stability while also allowing the size of the shape filter 220 to be reduced. In at least one example embodiment, the slope of the first surface 400 between the third region 510 and the second region 505 may be about 45° relative to a horizontal line extending through the first inflection point 630 perpendicular to the vertical axis 610. In other example embodiments, the slope may be greater than or less than 45°. The slope of the first surface 400 between the third region 510 and the first region 500 may be the same as the slope between the third region 510 and the second region 505 in some example embodiments.

In at least on example embodiment, the first region 500 and the second region 505 are mirror images across the vertical axis 610 of the shape filter 220. For example, the shape filter 220 may include a length 640 between the vertical axis 610 and the second side 620. A length between the vertical axis 610 and first side 615 of the shape filter may be the same as the length 640. The length 640 may be such that the entire radiation beam is covered by the shape filter 220. In at least one example embodiment, the length 640 is between about 0 cm and about 20 cm.

In at least one example embodiment, the shape filter 220 includes a first height 645 extending from the second surface 405 to tops of the first region 500 and the second region 505. The first height 645 of the shape filter may be between about 1 cm and about 20 cm. In at least one example embodiment, the shape filter 220 also includes a second height 650 between the second surface 405 and the base of the curved surface of the third region 510. For example, the second height 650 may be between about 0 mm and about 10 mm.

In at least one example embodiment, the geometry and dimensions of the shape filter 220 discussed above with respect to FIG. 5C improves the ease of manufacturing. The cost of manufacturing the shape filter 220 may also be reduced due to less material and less weight required to produce the shape filter 220. Additionally, the dimensions and shape of the shape filter 220 may be modified based on the desired filter effect. For example, the dimensions discussed above with respect to FIG. 5C, such as the radius 600, the length 640, the first height 645, and the second height 650, may be adjusted to suit a particular need.

While example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

We claim:

1. An apparatus comprising:
   a pre-collimator including,
   a first part, and
   a second part aligned with a central beam axis of a radiation beam, the second part being fixed with respect to the radiation beam, and the second part of the pre-collimator being closer to a source of the radiation beam than the first part of the pre-collimator; and a shape filter in at least a first portion of the first part of the pre-collimator.

2. The apparatus of claim 1, wherein:

the first part of the pre-collimator is configured to move between a first position and a second position;

the first portion is aligned with the central beam axis of the radiation beam in the first position; and the first portion is out of the radiation beam in the second position.

3. The apparatus of claim 2, wherein the first part of the pre-collimator comprises a second portion, the second portion similar to the first portion of the pre-collimator.

4. The apparatus of claim 3, wherein:

the second portion is aligned with the central beam axis of the radiation beam and the first portion is out of the radiation beam when the first part is in the second position; and the second portion is out of the radiation beam and the first portion is aligned with the central beam axis of the radiation beam when the first part is in the first position.

5. The apparatus of claim 3, further comprising:

a mount configured to hold the first portion and the second portion of the pre-collimator.

6. The apparatus of claim 5, wherein:

the mount is configured to move between the first position and the second position;

when the mount is in the first position, the first portion of the pre-collimator is aligned with the central beam axis; and when the mount is in the second position, the second portion of the pre-collimator is aligned with the central beam axis.

7. The apparatus of claim 5, further comprising:

a first beam hardening filter coupled to the mount adjacent the first portion of the pre-collimator; and a second beam hardening filter coupled to the mount adjacent the second portion of the pre-collimator.

8. The apparatus of claim 1, wherein the shape filter includes a first surface and a second surface opposite the first surface, the first surface includes a curved surface configured to face a radiation source, and the second surface comprises a planar surface.

9. A system comprising:

a radiation source configured to emit a radiation beam; and a filtering assembly, the filtering assembly including, a pre-collimator including, a first part, and a second part aligned with a central beam axis of the radiation beam, the second part being fixed with respect to the radiation beam, and the second part of the pre-collimator being closer to the radiation source than the first part of the pre-collimator, and a shape filter in at least a first portion of the first part of the pre-collimator.

10. The system of claim 9, wherein:

the first part of the pre-collimator is configured to move between a first position and a second position;

the first portion is aligned with the central beam axis of the radiation beam in the first position; and the first portion is out of the radiation beam in the second position.

11. The system of claim 10, wherein the first part of the pre-collimator comprises a second portion, the second portion similar to the first portion of the pre-collimator.

12. The system of claim 11, wherein:

the second portion is aligned with the central beam axis of the radiation beam and the first portion is out of the radiation beam when the first part is in the second position; and the second portion is out of the radiation beam and the first portion is aligned with the central beam axis of the radiation beam when the first part is in the first position.

13. The system of claim 11, further comprising:

a mount configured to hold the first portion and the second portion of the pre-collimator.

14. The system of claim 13, wherein:

the mount is configured to move between the first position and the second position;

when the mount is in the first position, the first portion of the pre-collimator is aligned with the central beam axis; and when the mount is in the second position, the second portion of the pre-collimator is aligned with the central beam axis.

15. The system of claim 13, further comprising:

a first beam hardening filter coupled to the mount adjacent the first portion of the pre-collimator; and a second beam hardening filter coupled to the mount adjacent the second portion of the pre-collimator.

16. The system of claim 9, wherein the shape filter includes a first surface and a second surface opposite the first surface, the first surface includes a curved surface configured to face the radiation source, and the second surface comprises a planar surface.

* * * * *